United States Patent [19]
Dittmar

[11] 3,969,370
[45] July 13, 1976

[54] 1-TERTIARY-ALKYL-3-(SUBSTITUTED FURYL)UREAS AS ANTIHYPERTENSIVE AGENTS

[75] Inventor: Bruce I. Dittmar, Wilmington, Del.

[73] Assignee: E. I. Du Pont de Nemours and Company, Wilmington, Del.

[22] Filed: Mar. 11, 1975

[21] Appl. No.: 555,306

Related U.S. Application Data

[63] Continuation-in-part of Ser. No. 461,700, April 17, 1974, abandoned.

[52] U.S. Cl. .................... 260/343.6; 71/28; 424/279
[51] Int. Cl.$^2$ ............................. C07D 307/30
[58] Field of Search ........................... 260/343.6

[56] References Cited
UNITED STATES PATENTS
R27,894  1/1974  Gerike et al. .................... 260/343.6

OTHER PUBLICATIONS
Petersen, Liebigs Ann. Chem. 726, pp. 89–99, (1969).

Primary Examiner—Henry R. Jiles
Assistant Examiner—C. M. S. Jaisle

[57] ABSTRACT

This invention relates to a class of 1-tertiary-alkyl-3-(substituted furyl)ureas that exhibit antihypertensive activity in warm-blooded animals. A representative compound is 1-tert-butyl-3-(2,5-dihydro-5-oxo-3-furyl)urea. This compound additionally possesses herbicidal activity.

8 Claims, No Drawings

1-TERTIARY-ALKYL-3-(SUBSTITUTED FURYL)UREAS AS ANTIHYPERTENSIVE AGENTS

CROSS REFERENCE TO RELATED APPLICATION

This application is a continuation-in-part of my co-pending application Ser. No. 461,700, filed Apr. 17, 1974, now abandoned.

BACKGROUND OF THE INVENTION

It is well known that certain guanidine derivatives of tert-carbinamines possess antihypertensive (hypotensive) activity. Specific examples are tert-alkyl cyanoguanidines such as 1-tert-amyl-3-cyanoguanidine, as described in S. M. Gadekar, S. Nibi, and E. Cohen, J. Med. Chem., 11 811 (1968); and various derivatives of tert-alkyl guanidines such as tert-butyl guanidines, as described in J. H. Short, C. W. Ours, W. J. Ranus, Jr., J. Med. Chem., 11 1129 (1968).

However, urea derivatives are not represented in comprehensive discussions of antihypertensive agents such as W. T. Comer and A. W. Gomoll, *Medicinal Chemistry*, Third Edition, A. Burger, Wiley-Interscience, New York, 1970, pp. 1019–1064; and *Medicinal Chemistry*, Volume 7, "Antihypertensive Agents", E. Schlittler, Academic Press, New York, 1967. The urea-derivative compounds of this invention provide effective treatment of hypertension, yet differ structurally and chemically over antihypertensive agents currently known. The representative compound 1-tert-butyl-3-(2,5-dihydro-5-oxo-3-furyl)urea additionally exhibits herbicidal activity as a growth retardant of certain plants.

SUMMARY OF THE INVENTION

This invention relates to (a) compounds represented by the formula

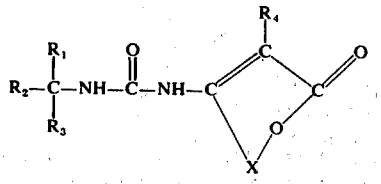

where
$R_1$, $R_2$, and $R_3$ are $C_1 - C_4$ alkyl, $C_2$-$C_4$ alkenyl, $C_2$-$C_4$ alkynyl, with the provisos that the total number of carbon atoms of $R_1$ plus $R_2$ plus $R_3$ does not exceed 6, that not more than one of $R_1$, $R_2$, or $R_3$ is alkynyl, and that two of $R_1$, $R_2$, and $R_3$ may be joined to form a cycloalkyl or cycloalkenyl group;
X is —$CH_2$—, methyl-substituted methylene, ethyl-substituted methylene, propyl-substituted methylene, or butyl-substituted methylene; and
$R_4$ is hydrogen or methyl with the proviso that when $R_4$ is methyl, X is methylene; and
(b) sodium, potassium or calcium salts of compounds of (a) wherein X is methylene, methyl-substituted methylene or ethyl-substituted methylene.

Preferred compounds within the scope of the above definition include those wherein $R_1$, $R_2$, and $R_3$ are $C_1$-$C_4$ alkyl and X is —$CH_2$— or —$CH(CH_3)$—.

The compounds of this invention are useful as antihypertensive agents when administered to warm-blooded animals. Additionally, the compound 1-tert-butyl-3-(2,5-dihydro-5-oxo-3-furyl)urea possesses growth retardant activity in plants.

DETAILED DESCRIPTION OF THE INVENTION

As indicated above, compounds of the invention include those of the formula

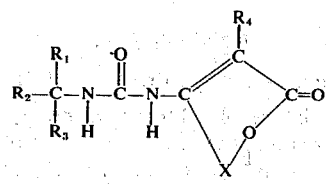

wherein
$R_1$, $R_2$, $R_3$, $R_4$ and X are as previously defined.

It is also to be understood that certain metal salts of the above-defined compounds are included within the scope of this invention. Illustrative of such metals are sodium, potassium and calcium.

The compounds of this invention are readily prepared as represented by the following equations:

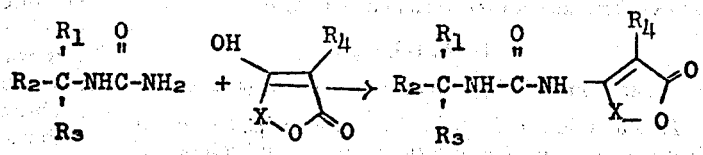

wherein $R_1$, $R_2$, $R_3$, $R_4$ and X are as defined above.

The compounds are prepared by heating equimolar amounts of the desired tertiary-alkylurea and the appropriate, 2,4-furandione in benzene with provision for water removal as, for example, a Dean-Stark water separator. In many cases water removal is not necessary. A catalytic amount of a strong acid (e.g., p-toluenesulfonic acid) is usually added to hasten the reaction. Although benzene is the preferred solvent, other solvents can be employed as, for example, toluene. Refluxing is continued until no more water is condensed in the Dean Stark trap. Often the product precipitates during the course of the reaction and can subsequently be removed by filtration. Otherwise, it is isolated by chromatography and/or crystallization.

Alternatively, many of the furanylureas of this invention can be prepared by heating equimolar amounts of the desired tertiary-alkylurea and the appropriate 4-haloalkanoylacetic acid ester (e.g., ethyl 4-bromoacetoacetate) with a catalytic amount of acid in refluxing benzene and with a water separator, following the procedure as outlined above.

EXAMPLE 1a 1-tert-butyl-3-(2,5-dihydro-5-oxo-3-furyl)urea

A stirred mixture of 4.65 g (0.04 mole) of tert-butylurea and 4.0 g (0.04 mole) of 2,4-furandione (tetronic acid) in 60 ml of benzene is refluxed in a flask equipped with a Dean-Stark water separator. Initially, a clear solution is formed; as the reaction proceeds, a heavy solid precipitates. When no more water gathers in the separator, the flask is allowed to cool to room temperature. The solid is collected by filtration, washed with either ether or benzene, and dried to give 6.7 g of solid, m.p. 175°–177°C. (dec.). Recrystallization from water-ethanol (60:40) produces 1-tert-butyl-3-(2,5-dihydro-5-oxo-3-furyl)urea, m.p. 197°–198°C.

Analysis:
| | | | | | | |
|---|---|---|---|---|---|---|
| Calcd. | C, | 54.53; | H, | 7.12; | N, | 14.13 |
| Found; | C, | 54.30; | H, | 7.63; | N, | 14.09 |
| | | 53.99; | | 7.43; | | 14.00 |

EXAMPLE 1b 1-tert-butyl-3-(2,5-dihydro-5-oxo-3-furyl)urea

A stirred mixture of 20.9 g (0.1 mole) of ethyl 4-bromoacetoacetate and 11.6 g (0.1 mole) of tert-butylurea in 200 ml of benzene is refluxed in a flask equipped with a Dean-Stark water separator until no more water separates. The flask is allowed to cool to room temperature. The solid is collected by filtration, washed with either ether or benzene, and dried to give 6.9 g (35%) of crystals, m.p. 189°–192°C. Two or three recrystallizations from water-alcohol as in Example 1a gives 3.9 g (20%) of 1-tert-butyl-3-(2,5-dihydro-5-oxo-3-furyl)urea, m.p. 196°–197°C. The infrared spectrum was identical with that from Example 1a and the mixture melting point was undepressed. The nmr spectrum was consistent with the assigned structure.

EXAMPLE 2

1-tert-amyl-3-(2,5-dihydro-5-oxo-3-furyl)urea

To a solution of 3 g of 2,4-furandione in 100 ml of benzene is added 4 g of tert-amylurea. The solution is heated under nitrogen at reflux for 3 hours with water removal. At the end of that period the solution is cooled and concentrated. The residual material is recrystallized from acetonitrile to give 2.5 g of 1-tert-amyl-3-(2,5-dihydro-5-oxo-3-furyl)urea, m.p. 169°–171°C. The infrared and n.m.r. spectra are consistent with the assigned structure.

EXAMPLE 3

1-(1-methylcyclopentyl)-3-(2,5-dihydro-5-oxo-3-furyl)urea

Using the procedure described in Example 2 using 3 gm of 2,4-furandione and 4 g of 1-methylcyclopentylurea there is obtained 3 g of 1-(1-methylcyclopentyl)-3-(2,5-dihydro-5-oxo-3-furyl)urea, m.p. 170°C. (decomposition).

EXAMPLE 4

1-(1-methylcyclohexyl)-3-(2,5-dihydro-5-oxo-3-furyl)urea

Using the procedure described in Example 2 using 5 g of 2,4-furandione and 6 g of 1-methylcyclohexylurea there is obtained 3.5 g 1-(1-methylcyclohexyl)-3-(2,5-dihydro-5-oxo-3-furyl)urea, m.p. 183°C. (decomposition).

EXAMPLE 5

1-(1,1-dimethylpropargyl)-3-(2,5-dihydro-5-oxo-3-furyl)urea

To a solution of 5 g 2,4-furandione in 100 ml benzene there is added 6 g of 1,1-dimethylpropargylurea. The solution is heated at reflux under nitrogen for 3 hours with water removal. At the end of this period, the solution is cooled and concentrated. The residual material is dissolved in 25 ml of ethyl acetate and filtered. The filtrate is chromatographed on 150 g of silicic acid. Elution with a solution of benzene (60%), ethyl acetate (30%) and methanol (10%), gives crystalline material. Recrystallizations of this material from acetonitrile gives 2.5 g of 1-(1,1-dimethylpropargyl)-3-(2,5-dihydro-5-oxo-3-furyl)urea, m.p. 178°C. (decomposition).

EXAMPLE 6

1-(1,1-dimethylbutyl)-3-(2,5-dihydro-5-oxo-3-furyl)urea

To a solution of 22 g of methyl-4-bromoacetoacetate in 200 ml benzene is added 14.4 g of 1,1-dimethylbutylurea and 100 mg of p-toluenesulfonic acid. The solution is heated at reflux under nitrogen for 4 hours with water removal. At the end of this period the solution is cooled and concentrated. The residual material is chromatographed on 400 g of silicic acid. Elution with a solution of benzene (60%), ethyl acetate (30%) and methanol (10%) gives crystalline material. Recrystallization of this material from ethyl acetate gives 1.8 g of 1-(1,1-dimethylbutyl)-3-(2,5-dihydro-5-oxo-3-furyl)urea, m.p. 130°–132°C.

EXAMPLES 7–15

Using the procedure described in Example 5, reacting the compound

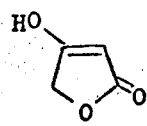

with the indicated respective reactants of column 1, below, using a trace of p-toluenesulfonic acid if desired, produces the respective compounds of this invention as shown in column 2.

| Example | Reactant | Product |
|---|---|---|
| 7 | CH₂=C(CH₃)—C(CH₃)₂—N(H)—C(O)—NH₂ | CH₂=C(CH₃)—C(CH₃)₂—N(H)—C(O)—N(H)-furyl<br>m.p. 167°C. (dec.) |
| 8 | CH₂=CH—CH₂—C(CH₃)₂—NHC(O)—NH₂ | CH₂=CH—C(H)(CH₃)—C(CH₃)—N(H)—C(O)—N(H)-furyl |

-continued
| Example | Reactant | Product |
|---|---|---|
| 9 | 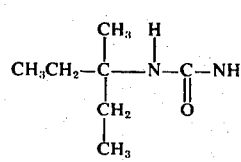 | 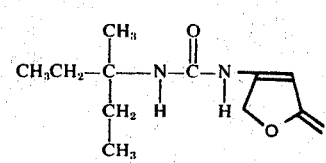 m.p. 145°C. (dec.) |
| 10 | 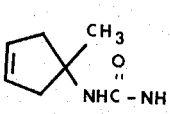 | 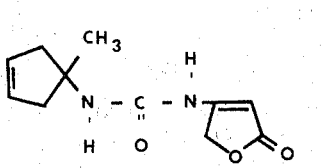 |
| 11 | 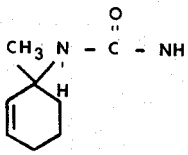 | 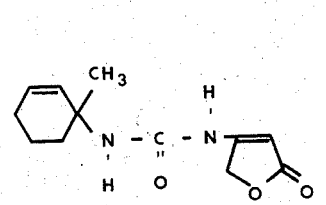 |
| 12 | 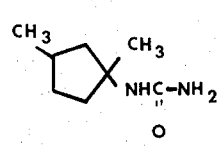 | 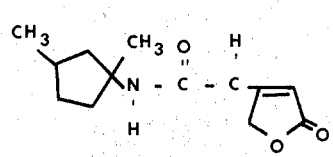 |
| 13 | 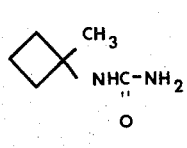 | 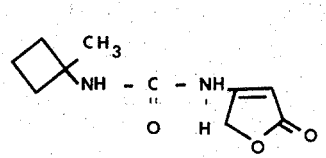 |
| 14 | 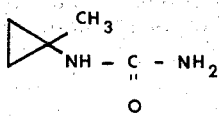 | 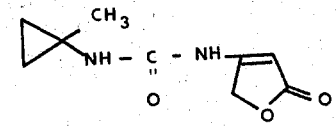 |
| 15 | 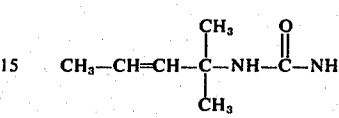 | 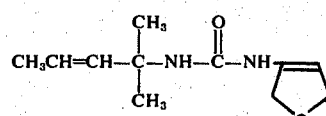 |
EXAMPLES 16–20
Using the procedure as described in Example 5, reacting the compound
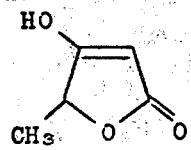
with the indicated respective reactants of column 1, below, using a trace of p-toluenesulfonic acid if desired, produces the respective compounds of this invention as shown in column 2.

| Example | Reactant | Product |
|---|---|---|
| 16 | CH₃—C(CH₃)(CH₃)—NHCNH₂ ‖O | CH₃—C(CH₃)(CH₃)—NHC(O)—NH—[5-methyl-2(5H)-furanone-4-yl] m.p. 204–205°C. (dec.) |
| 17 | 1-methylcyclopropyl-NHCNH₂ ‖O | 1-methylcyclopropyl-NH—C(O)—NH—[5-methyl-2(5H)-furanone-4-yl] |
| 18 | 1-methylcyclobutyl-NHCNH₂ ‖O | 1-methylcyclobutyl-NH—C(O)—NH—[5-methyl-2(5H)-furanone-4-yl] |
| 19 | 1-methylcyclopentyl-NHC(O)NH₂ | 1-methylcyclopentyl-NH—C(O)—NH—[5-methyl-2(5H)-furanone-4-yl] |
| 20 | CH₂=C(H)—C(CH₃)(CH₃)—NHC—NH₂ ‖O | CH₂=C(H)—C(CH₃)(CH₃)—NH—C(O)—NH—[5-methyl-2(5H)-furanone-4-yl] |

EXAMPLES 21–23

Using the procedure as described in Example 5, reacting the compound

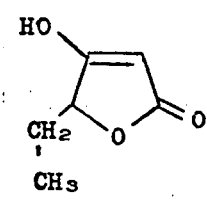

with the indicated respective reactants of column 1, below, using a trace of p-toluenesulfonic acid if desired, produces the respective compounds of this invention as shown in column 2.

| Example | Reactant | Product |
|---|---|---|
| 21 | 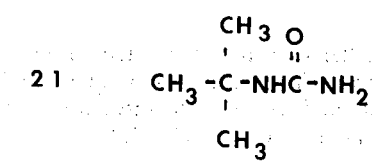 | 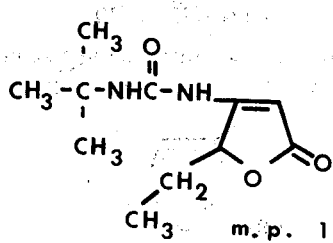 m.p. 145–146°C. |

| Example | Reactant | Product |
|---------|----------|---------|
| 22 | 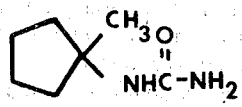 | 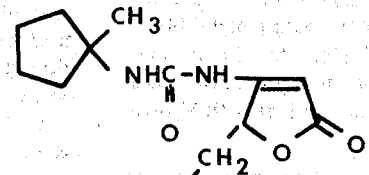 |
| 23 | 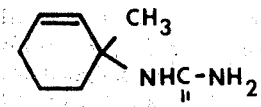 | 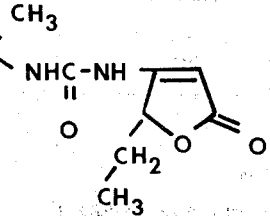 |

EXAMPLE 24

1-tert-butyl-3(2,5-dihydro-5-oxo-2-n-propyl)-3-furyl)urea

A mixture of 7.1 g. of 5-n-propyl-2,4-furandione [Conrad and Gast, Chem. Ber 31. 2726 (1896)], 6.0 g. of tert-butylurea, and 0.2 g. of p-toluenesulfonic acid is refluxed in benzene for 8 hours. The mixture is cooled, and the benzene removed by evaporation. The residue is triturated with dilute sodium hydroxide solution and ether. The solid is filtered off and identified as unchanged tert-butylurea. The ether solution is dried and evaporated. The residue is chromatographed on silicic acid with 60:40 mixture of toluene and ethyl acetate respectively to give 1-tert-butyl-3(2,5-dihydro-5-oxo-2-n-propyl)-3-furyl)urea. The structure is confirmed by infrared and n.m.r. spectra and elemental analysis.

EXAMPLE 25

1-tert-butyl-3(2-n-butyl-2,5-dihydro-5-oxo-3-furyl)urea 5-n-Butyl-2,4-furandione, is made by the method of Benary for preparing substituted 2,4-furandiones [Chem. Ber. 40, 1079 (1907)], as follows:

(1) 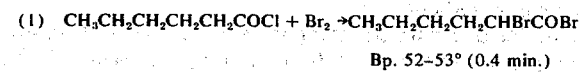

Bp. 52–53° (0.4 min.)

(2) 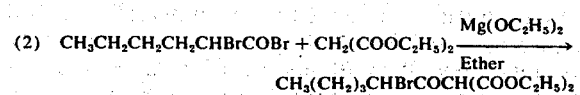

(3) 

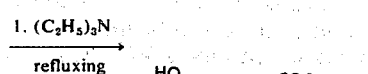

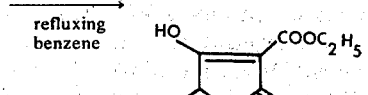

m.p. 72–73°

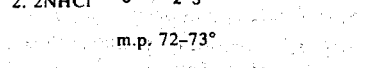

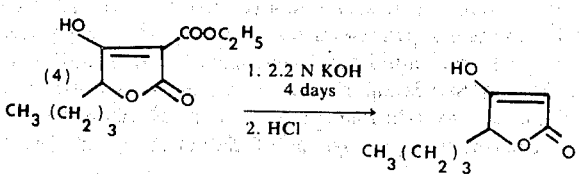

The procedure of Example 24 is followed using 5-n-butyl-2,4-furandione in place of 5-n-propyl-2,4-furandione. The 1-tert-butyl-3(-2-m-butyl-2,5-dihydro-5-oxo-3-furyl)urea so formed, melts at 125°–126° (preliminary sintering). The structure is confirmed by infrared and n.m.r. spectra and elemental analysis.

EXAMPLE 26

1-tert-butyl-3(2,5-dihydro-4-methyl-3-furyl)urea

A mixture of 30.4 g. of 3-methylfurandione [prepared as described by Svendsen and Boll, Tetrahedron 29, 4251 (1973)], in 200 ml. of benzene is refluxed for 16 hours. The mixture is cooled, and the benzene removed by evaporation. The residue is triturated with dilute potassium bicarbonate solution. The solid is filtered off and was triturated with 50 ml. of 10% sodium hydroxide solution. The solid is filtered off and the filtrate is acidified to ph <1 with 6N HCl. The solution on cooling and standing deposits crystals. For example, m.p. 253°–254° (dec) are identified as 1-tert-butyl-3(2,5-dihydro-4-methyl-3-furyl)urea by infrared and n.m.r. spectra and elemental analysis.

EXAMPLE 27 sodium salt of 1-tert-butyl-3(2,5-dihydro-5-oxo-3-furyl)urea

To a solution of 0.8 g. of sodium hydroxide in 150 ml. of methanol is added 4.0 g. of 1-tert-butyl-3(2,5-dihydro-5-oxo-3-furyl)urea. The mixture is stirred until homogeneous and then is evaporated to leave a glassy residue of the sodium salt. The structure is confirmed by the infrared and n.m.r. spectra. For example, the peak for the acidic NH in the n.m.r. spectrum of 1-tert-butyl-3-(2,5-dihydro-5-oxo-3-furyl)urea is found at 9.2 p.p.m. but in the sodium salt is absent. 1-Tert-butyl-3-(2,5-dihydro-5-oxo-3-furyl)urea is useful as a plant growth retardant. It may be used to retard the growth of brush under power lines and along rights-of-way. The rates used will vary from 1 to 50 kg/ha depending upon the species to be treated, the duration of retardation desired, the climate, and other environmental factors. One with ordinary skill in the art may select the rate to be used without difficulty.

It also may be used to retard the growth of cotton late in the season, thus making it easier to harvest the crop. The rates used are in the range of 1–10 kg/ha depending on the climate, the cotton variety, and the duration of retardation desired. One with ordinary skill in the art may select the rate to be used.

The following tests demonstrate the utility of this compound as a growth retardant.

EXAMPLE A

Privet (*Ligustrum sp.*), approximately 40 cm tall, was treated with a foliar spray of the test chemical dissolved in a non-phytotoxic solvent. The treated plants and similar controls were maintained in a greenhouse for eight weeks, then the visual ratings of growth shown below were taken.

| Rate, kg/ha | Plant Response |
| --- | --- |
| 0 | 0 |
| 1.1 | 3G |
| 4.4 | 4G |
| 0 | 0 |

G = Growth retardation
0 = No response; 10 = maximum response

EXAMPLE B

Foliage of cotton five weeks old and having five leaves was treated with the test chemical in a non-phytotoxic solvent. The treated plants and controls were placed in a greenhouse for 16 days then observed and rated for response. The table below shows the results:

| Rate, kg/ha | Plant Response |
| --- | --- |
| 0 | 0 |
| 1.1 | 5G,1C |
| 5.5 | 8G,1C |

G = Growth retardation; C = chlorosis, necrosis
0 = No response; 10 = maximum response The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively, or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health, and weight of the receipient, the extent of disease, kind of concurrent treatment, if any, frequency of treatment, and the nature of the effect desired. Usually, a daily dosage of active ingredient compound will be from about 0.1 to 50 milligrams per kilogram of body weight. Ordinarily, from 0.5 to 40, and preferably 1.0 to 20, milligrams per kilogram per day in one or more applications per day is effective to obtain desired results. For the more potent compounds of the invention, e.g., 1-tert-butyl-3-(2,5-dihydro-5-oxo-3-furyl)urea, the daily dosage ranges are from about 0.1 to 20 mg/kg, preferably 0.5 to 15 mg/kg, and more preferably 1.0 to 10 mg/kg.

The antihypertensive activity of the compounds of this invention is evidenced by tests conducted in hypertensive rats and by further tests which show a blood pressure lowering effect in normotensive dogs.

In these tests rats are made hypertensive by repeated injections of desoxycorticosterone acetate (DOCA) and by giving the rats saline solution to drink essentially according to the method described by Stanton and White [Arch. Intern. Pharmacodyn., 154, 351 (1965)]. Graded dose levels of each compound are administered orally to groups of eight hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by a modification of the microphone-manometer technique [Friedman, M. and Freed, S. C., Proc. Soc. Exp. Biol. and Med., 70, 670 (1959)]. That dose of compound which produces a 30 mm mercury (mm Hg) reduction in blood pressure when compared to the mean systolic arterial blood pressure of the control animals is then determined (Effective Dose 30). For example, an ED30 of 2.5 mg/kg orally was obtained with 1-tert-butyl-3-(2,5-dihydro-5-oxo-3-furyl)urea. ED30's of 4.2, 4.9, 2.0, and 2.5 were obtained with 1-(1-methylcyclopentyl)-3-(2,5-dihydro-5-oxo-3-furyl)urea, 1-(1,1-dimethylpropargyl)-3-(2,5-dihydro-5-oxo-3-furyl)urea, and 1-tert-amyl-3-(2,5-dihydro-5-oxo-3-furyl)urea, and 1-(1,1-dimethylbutyl)-3-(2,5-dihydro-5-oxo-3-furyl)urea, respectively.

In a test involving dogs, these compounds are administered intravenously (i.v.) to eight anesthetized normotensive dogs according to a cumulative dose schedule. Arterial blood pressure is recorded directly through an arterial cannula and a polygraph by which it is determined that the compound shows statistically significant blood pressure lowering in comparison to the predosing control value and to the effect of vehicle on control animals.

The compounds of this invention can be employed in useful pharmaceutical compositions according to the present invention in such dosage forms as tablets, capsules, powder packets, or liquid solutions, suspensions or elixirs for oral administration or liquid for parenteral use, and in certain cases, suspensions for parenteral use (except intravenous injections). In such compositions, the active ingredient will ordinarily always be present in an amount of at least 0.5% by weight based on the total weight of the composition and not more than 95% by weight.

Besides the active ingredient compound of this invention, the antihypertensive composition will contain a solid or liquid non-toxic pharmaceutical carrier for the active ingredient.

In one embodiment of a pharmaceutical composition of this invention, the solid carrier is a capsule which can be of the ordinary gelatin type. In the capsules will be from about 5 to 90% by weight of a compound of the invention and 95 to 10% of a carrier. In another embodiment, the active ingredient is tableted with or without adjuvants. In yet another embodiment, the active ingredient is put into powder packets and employed. These capsules, tablets, and powders will generally constitute from about 1 to about 95% and preferably from 5 to 90% by weight of active ingredient. These dosage forms preferably contain from about 5 to about 500 milligrams of active ingredient, with about 7 to about 250 most preferred.

The pharmaceutical carrier can, as previously indicated, be a sterile liquid such as water and oil, including those of petroleum, animal, vegetable oils of synthetic origin, for example, peanut oil, soybean oil, mineral oil, sesame oil, and the like. In general, water saline, aqueous dextrose (glucose) and related sugar solutions and glycols such as propylene glycol or polyethylene glycols are preferred liquid carriers, particularly for injectible solutions. Sterile injectible solutions, such as saline, will ordinarily contain from about 0.5 to 25% and preferably about 1 to 10% by weight of the active ingredient.

As mentioned above, oral administration can be in a suitable suspension or syrup, in which the active ingredient ordinarily will constitute from about 0.7 to 10% and preferably about 1 to 5%, by weight. The pharmaceutical carrier in such composition can be a watery vehicle such as an aromatic water, a syrup, or a pharmaceutical mucilage.

Suitable pharmaceutical carriers are described in "Remington's Pharmaceutical Sciences" by E. W. Martin, a well-known reference text in this field.

The following examples will further illustrate the preparation of pharmaceutical compositions of the invention.

EXAMPLE C

A large number of unit capsules are prepared by filling standard two-piece hard gelatin capsules each with 250 milligrams of powdered 1-tert-butyl-3-(2,5-dihydro-5-oxo-3-furyl)urea, 110 milligrams of lactose, 32 milligrams of talc, and 8 milligrams of magnesium stearate.

EXAMPLE D

A mixture of 1-tert-amyl-3-(2,5-dihydro-5-oxo-3-furyl)urea in soybean oil is prepared and injected by means of a positive displacement pump into gelatin to form soft gelatin capsules containing 35 milligrams of the active ingredient. The capsules are washed in petroleum ether and dried.

EXAMPLE E

A large number of tablets are prepared by conventional procedures so that the dosage unit is 100 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch, and 98.8 milligrams of lactose. Appropriate coatings may be applied to increase palatability or delay absorption.

EXAMPLE F

A parenteral composition suitable for administration by injection is prepared by stirring 1.5% by weight of 1-(1-methylcyclopentyl)-3-(2,5-dihydro-5-oxo-3-furyl)urea in 10% by volume propylene glycol and water. The solution is sterilized by filtration.

EXAMPLE G

An aqueous suspension is prepared for oral administration so that each 5 milliliters contain 50 milligrams of finely divided 1-tert-butyl-3-(2,5-dihydro-5-oxo-3-furyl)urea, 500 milligrams of acacia, 5 milligrams of sodium benzoate, 1.0 grams of sorbitol solution, U.S.P., 5 milligrams of sodium saccharin, and 0.025 milliliters of vanilla tincture.

EXAMPLE H

A parenteral composition suitable for administration by injection is prepared by dissolving 1% by weight of 1-(tert-butyl)-3-(2,5-dihydro-5-oxo-3-furyl)urea in sodium chloride injection U.S.P. XV and adjusting the ph of the solution to between 6 and 7. The solution is sterilized by filtration.

A wide variety of compositions coming within this invention can be prepared by substituting other compounds of this invention, including specifically but not limited to those compounds named hereinbefore for the compounds named in Examples C-H above and substituting other suitable pharmaceutical carriers well known and described in the Martin text mentioned above.

What is claimed is:

1. A compound selected from
a. compounds of the formula

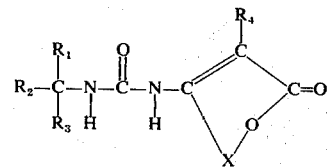

where
$R_1$, $R_2$, and $R_3$ are $C_1$–$C_4$ alkyl, $C_2$–$C_4$ alkenyl, $C_2$–$C_4$ alkynyl, with the provisos that the total number of carbon atoms of $R_1$ plus $R_2$ plus $R_3$ does not exceed 6, that not more than one of $R_1$, $R_2$, or $R_3$ is alkynyl, and that two of $R_1$, $R_2$, and $R_3$ may be joined to form a cycloalkyl or cycloalkenyl group;

X is —$CH_2$—, methyl-substituted methylene, ethyl-substituted methylene, propyl-substituted methylene, or butyl-substituted methylene; and $R_4$ is hydrogen or methyl with the proviso that when $R_4$ is methyl, X is methylene; and b. sodium, potassium or calcium salts of compounds of (a) wherein X is methylene, methyl-substituted methylene, or ethylsubstituted methylene.

2. A compound of claim 1, wherein $R_1$, $R_2$, and $R_3$ are $C_1$–$C_4$ alkyls.

3. The compound of claim 1 which is 1-tert-butyl-3-(2,5-dihydro-5-oxo-3-furyl)urea.

4. The compound of claim 1 which is 1-tert-amyl-3-(2,5-dihydro-5-oxo-3-furyl)urea.

5. The compound of claim 1 which is 1-(1-methylcyclopentyl)-3-(2,5-dihydro-5-oxo-3-furyl)urea.

6. The compound of claim 1 which is 1-(1,1-dimethylpropargyl)-3-(2,5-dihydro-5-oxo-3-furyl)urea.

7. The compound of claim 1 which is 1-(1-methylcyclohexyl)-3-(2,5-dihydro-5-oxo-3-furyl)urea.

8. The compound of claim 1 which is 1-(1,1-dimethylbutyl)-3-(2,5-dihydro-5-oxo-3-furyl)urea.

* * * * *